United States Patent
Schuele

(10) Patent No.: US 7,357,570 B2
(45) Date of Patent: Apr. 15, 2008

(54) METHOD AND DEVICE FOR CONTACTLESS TEMPERATURE MONITORING AND TEMPERATURE ADJUSTMENT

(75) Inventor: Georg Schuele, Menlo Park, CA (US)

(73) Assignee: Medizinisches Laserzentrum Luebeck GmbH, Luebeck (DE)

( * ) Notice: Subject to any disclaimer, the term of this patent is extended or adjusted under 35 U.S.C. 154(b) by 43 days.

(21) Appl. No.: 10/542,298

(22) PCT Filed: Jan. 11, 2004

(86) PCT No.: PCT/DE2004/000018

§ 371 (c)(1),
(2), (4) Date: Jan. 9, 2006

(87) PCT Pub. No.: WO2004/065923

PCT Pub. Date: Aug. 5, 2004

(65) Prior Publication Data

US 2006/0233216 A1 Oct. 19, 2006

(30) Foreign Application Priority Data

Jan. 16, 2003 (DE) ................. 103 01 416

(51) Int. Cl.
*G01J 5/00* (2006.01)
*A61B 5/00* (2006.01)
*G01N 21/85* (2006.01)
*G01N 21/47* (2006.01)
*G01N 21/63* (2006.01)

(52) U.S. Cl. ............ 374/120; 374/129; 374/130; 600/549; 600/474; 356/35.5; 356/450; 356/953; 356/947; 356/949

(58) Field of Classification Search .......... None
See application file for complete search history.

(56) References Cited

U.S. PATENT DOCUMENTS

| | | | | | |
|---|---|---|---|---|---|
| 3,936,849 | A | * | 2/1976 | Tsujimoto | ............ 396/51 |
| 4,245,507 | A | * | 1/1981 | Samulski | ............ 374/159 |
| 4,650,302 | A | * | 3/1987 | Grant | ............ 351/206 |
| 4,653,855 | A | * | 3/1987 | Birnbach et al. | ........ 324/310 |
| 4,758,081 | A | * | 7/1988 | Barnes | ............ 606/4 |
| 4,807,633 | A | * | 2/1989 | Fry | ............ 600/438 |
| 4,973,149 | A | * | 11/1990 | Hutchinson | ......... 351/210 |
| 5,240,006 | A | * | 8/1993 | Fujii et al. | ............ 600/425 |

(Continued)

FOREIGN PATENT DOCUMENTS

WO    WO 01/26591    4/2001

*Primary Examiner*—Gail Verbitsky
(74) *Attorney, Agent, or Firm*—Larson & Larson; James E. Larson

(57) ABSTRACT

A method and device for determining the temperature of a sample, wherein a probing light beam is directed onto the sample whereby at least two partial beams of the probing light pass through paths of different lengths inside the sample by backscattering or reflecting the beams from at least two different depths in the sample, returning the partial beams to an analysis unit, and producing an interference pattern in the analysis unit by means of an interferometric device which uses one light beam as a reference for evaluating the interference pattern in an evaluating unit, wherein the signal intensity of the partial beam is determined counter to the optical path and the temperature displacement and temperature of the sample are determined by the temperature adjustment of the signal intensity.

9 Claims, 5 Drawing Sheets

U.S. PATENT DOCUMENTS

| | | | |
|---|---|---|---|
| 5,263,776 A * | 11/1993 | Abraham et al. | 374/161 |
| 5,347,327 A * | 9/1994 | Sekine et al. | 351/211 |
| 5,481,359 A * | 1/1996 | Barker | 356/519 |
| 5,710,630 A * | 1/1998 | Essenpreis et al. | 356/479 |
| 6,067,371 A * | 5/2000 | Gouge et al. | 382/128 |
| 6,091,496 A * | 7/2000 | Hill | 356/491 |
| 6,226,089 B1 * | 5/2001 | Hakamata | 356/432 |
| 6,437,859 B1 * | 8/2002 | Ohtomo et al. | 356/139.07 |
| 6,485,413 B1 * | 11/2002 | Boppart et al. | 600/160 |
| 6,580,448 B1 * | 6/2003 | Stuttler | 348/46 |
| 6,830,567 B2 * | 12/2004 | Schuele et al. | 606/4 |
| 6,900,943 B2 * | 5/2005 | Andersen et al. | 359/618 |
| 7,041,063 B2 * | 5/2006 | Abreu | 600/549 |
| 7,115,120 B2 * | 10/2006 | Lin | 606/4 |
| 7,184,148 B2 * | 2/2007 | Alphonse | 356/479 |
| 2002/0085208 A1 * | 7/2002 | Hauger et al. | 356/479 |
| 2006/0084948 A1 * | 4/2006 | Rovati et al. | 606/4 |
| 2006/0103724 A1 * | 5/2006 | Jongsma et al. | 348/78 |

\* cited by examiner

METHOD AND DEVICE FOR CONTACTLESS TEMPERATURE MONITORING AND TEMPERATURE ADJUSTMENT

RELATED APPLICATIONS

This is application is a National Stage filed under 35 USC § 371 of PCT Application No. PCT/DE2004/000018 filed Jan. 11, 2004, which claims priority under 35 USC § 119, to German Application No. 10301416.0 filed Jan. 16, 2003, the entire disclosures of which are hereby expressly incorporated by reference.

BACKGROUND OF THE INVENTION

1. Field of the Invention

The invention relates to a method and to a device for monitoring and controlling the temperature of a sample by determining its temperature-dependent refractive index.

Obvious applications of the present invention occur in the field of medical interventions, where e.g. by means of electromagnetic radiation, particularly laser light, temperature rises can be produced and simultaneously monitored and controlled in a biological tissue, e.g. in the retina of the eye.

2. Description of Prior Art

DE 199 35 455 A1 discloses a method and a device for planned heat deposition in a biological material. For this purpose ultrasonic waves are fed into a tissue and detected in time and space-resolved manner at an appropriate location. From a computer-assisted analysis of the emerging waves, particularly the degree of their relative transit time changes, information is obtained on the thermal and structural changes within the material, which are in turn used for controlling the heat quantity introduction, e.g. per laser light.

This method is not very suitable for ophthalmology due to the lack of space resolution with low frequency ultrasound and due to the strong sound absorption with high resolving, high frequency ultrasound and low power. However, there is a risk of damage to the sensitive retinal tissue in the case of strong excitation with mechanical waves.

It is obvious when measuring the temperature in the eye to make use of mainly optical methods, such as is e.g. implemented with known infrared ear thermometers. However, the vitreous body of the eye absorbs infrared light, so that it has hitherto been impossible to simply adapt such a thermometer for ophthalmological purposes.

DE 101 35 944 A1 discloses a device, in which a low power probing laser ensures a brief expansion of the tissue to be treated using regular light pulses. The expansion leads to the transmission of a pressure wave, which runs through the vitreous body and can be externally detected by means of a contact lens. The sensor acts as an ultrasonic receiver and transmits its data to a computer, which in turn controls the energy supply of a power laser.

DE 102 40 109 A1 describes another method, in which the temperature of the fundus oculi is determined by exciting to fluoresce. Changes to the spectral composition, the intensity or decay time of the fluorescent light are linked with a temperature rise compared with the normal level (approximately 37° C.). The fluorescent activity is due to dyes, which are either naturally concentrated with rising age in the eye, such as e.g. lipofuscin, or are introduced into the eye for medical treatment purposes.

An indirect access to the temperature of a sample is provided by the dependence of the refractive index on the sample temperature documented for numerous substances in the literature. Of particular interest for the biological tissue is the refractive index of water, which is described in summary form in the work by Thormahlen, Straub and Grigull, "Refractive Index of Water and its Dependence on Wavelength, Temperature and Density", J. Phys. Chem. Ref. Data. 14, 933-944 (1985). However, in practical terms the refractive index-based temperature measurement is hardly used, because virtually always simpler and more precise alternatives are available.

U.S. Pat. No. 4,468,136 describes a method for measuring the temperature distribution in the surface-near area of a sample under the action of a locally defined laser beam vertically striking the sample. Use is made of the formation of a thermal lens in the material, i.e. as a result of local temperature gradients there is a space-dependent differentiation of the refractive index and light is then deflected in glancing or surface-parallel incidence. The extent and direction of the deflection are dependent on the position and propagation direction of the "probing" light beam relative to the heating centre by the power laser.

The prerequisite for performing the method is an at least extensive transparency of the material for the probing light, particularly low absorption and low scattering, along the sample surface. In the case of biological samples this can only be achieved with high energy light, so that, apart from apparatus difficulties, there are objections to this method from the medical standpoint.

DE 39 29 290 A1 describes a measuring cell with which inter alia the ambient temperature of the cell is determined via the change to the optical path length for laser light in a medium with temperature-dependent refractive index in the interior of the cell. This change is determined interferometrically according to the known principle of interference on layers, in which the transit time difference between reflected partial beams of two parallel, optionally partly reflecting interfaces (such as the refracting medium) is measured and interpreted.

However, specifically DE 39 29 290 A1 is based on the precise knowledge of the refractive index as a function n(T,p,) by the design-side presetting of the refracting medium and the "good thermal contact" of said medium with the environment.

Non-invasive methods for determining light transit time distributions, particularly of infrared light in the biological tissue, are known as "Optical Coherence Tomography" (OCT). Thus, DE 199 29 406 A1 describes a device which simulates the transit time distribution by means of a structure based on the known double slit experiment in a detection unit in the form of an interferogram. For this purpose, initially short coherence length light is split up into a reference beam and a sample beam using a dichroic mirror. Whereas the reference light is reflected on a suitably spaced mirror, the sample light undergoes backscattering in different layer depths of a sample to be investigated.

Both reflected and backscattered light are supplied by light guides to the detection unit and as a result of spaced emergence there (cf. two point sources) projected in an at least partly overlapping manner onto a detector plane. This leads to an interference pattern, whose intensity course along the axis linking the light sources enables conclusions to be drawn concerning the light transit times within the sample.

The problem of the invention is to provide a method and a device permitting the contactless temperature measurement of a sample, whose emitted thermal radiation is inadequate for temperature measurement, without there being a thermal contact with a temperature sensor.

SUMMARY OF INVENTION

According to the invention this problem is solved by directing at least two partial beams of the probing light beam having different path lengths in the sample onto the latter, returning the reflected or backscattered partial beams to an analytical unit and evaluating the interference pattern produced in an evaluating unit, as well as by a device for performing the method.

BRIEF DESCRIPTION OF THE DRAWINGS

The invention is explained hereinafter relative to the attached drawings, wherein show.

DETAILED DESCRIPTION OF THE PREFERRED EMBODIMENT

Figure 1:
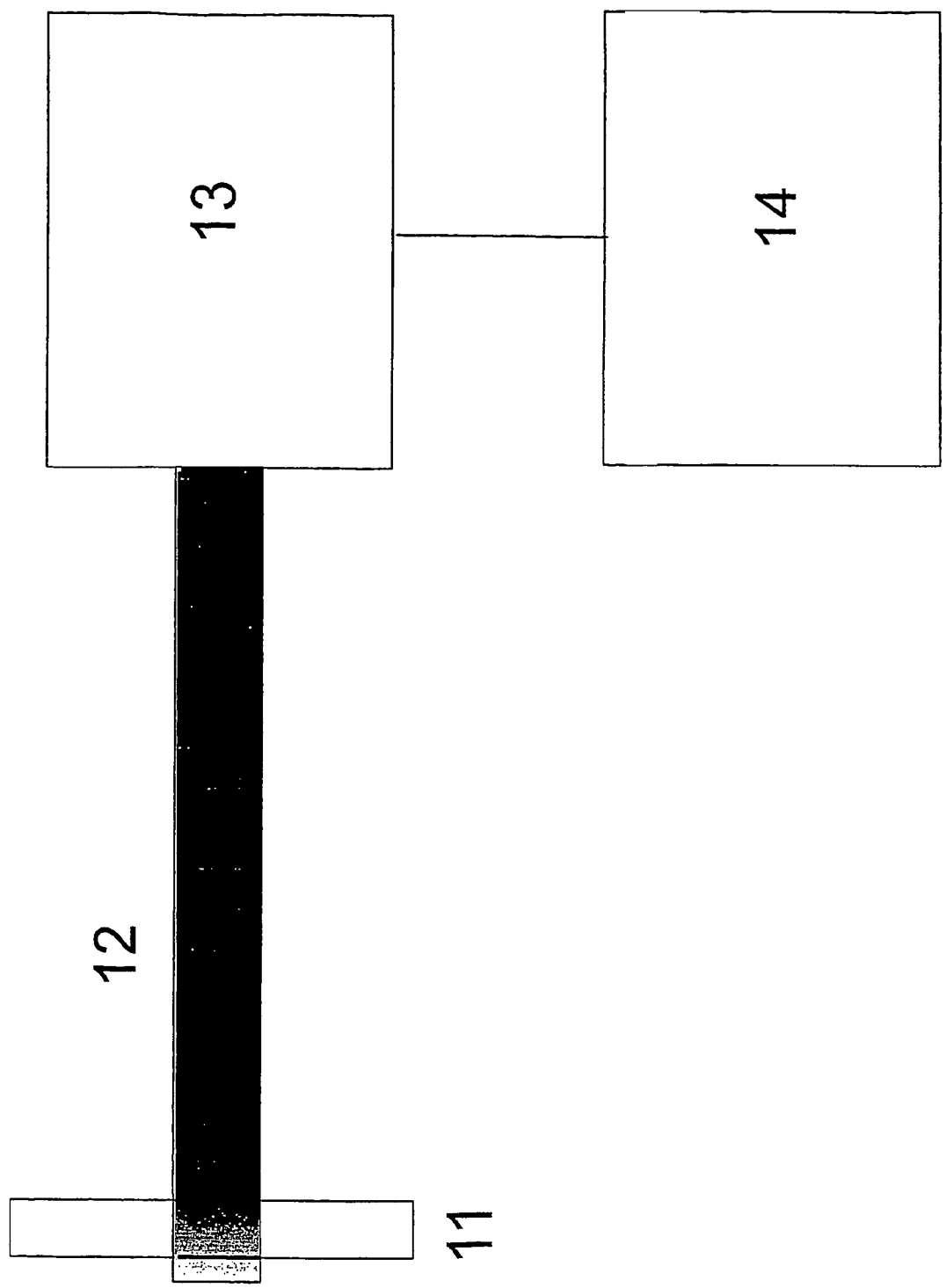
FIG. 1 The diagrammatic structure of the device for determining the temperature of a sample.

The device diagrammatically shown in FIG. 1 comprises a beam source producing a measuring beam 12 and an analyzer 13 (e.g. an OCT, spectral analyzer or white light interferometer) and an evaluating unit 14 used for determining the temperature of a sample 11.

Figure 2:
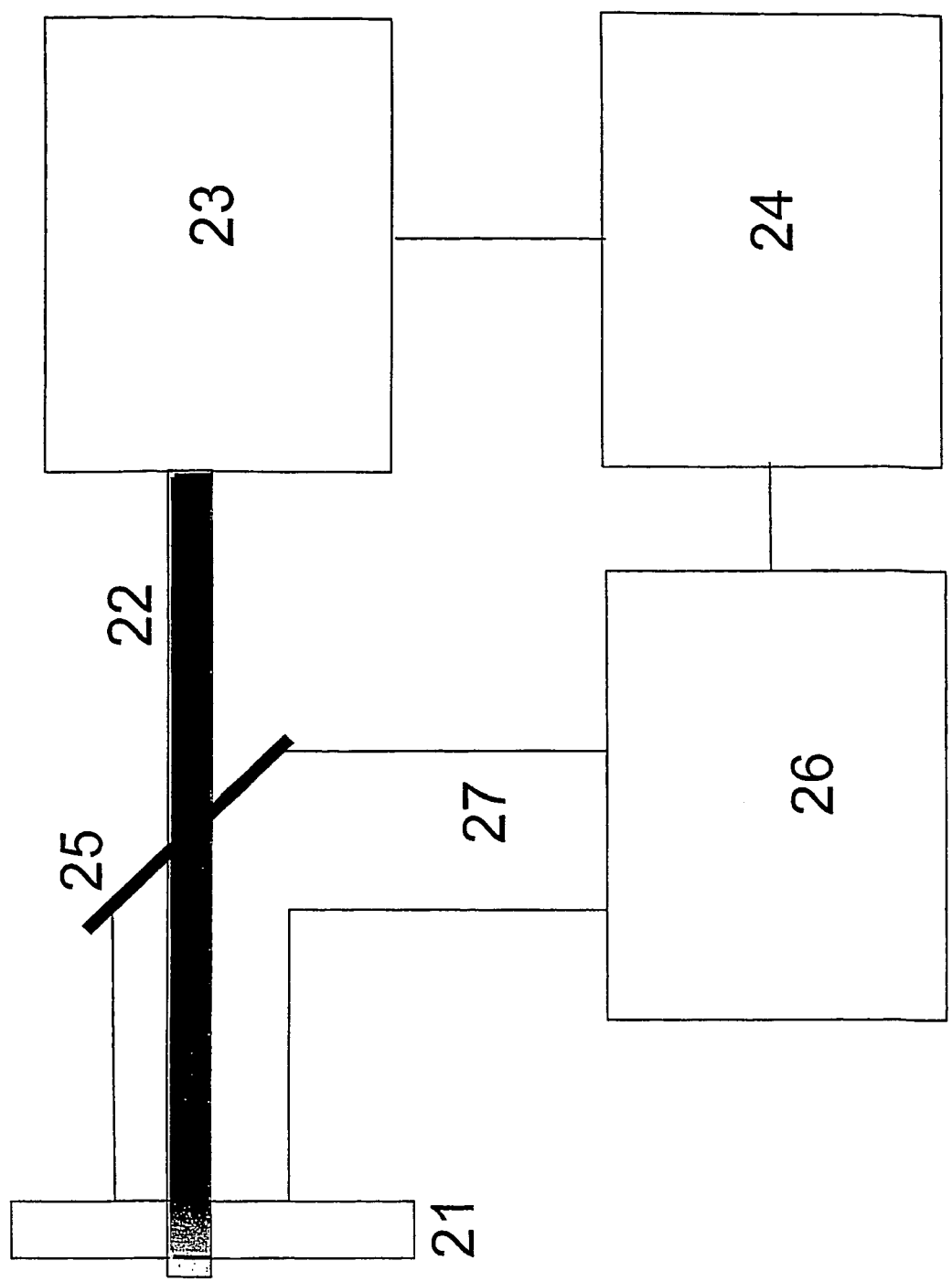
FIG. 2 The diagrammatic structure of the device for determining and controlling the temperature of a sample.

The device shown in FIG. 2 comprises a beam source producing a measuring beam 22 with an analyzer 24 (e.g. OCT, spectral analyzer, white light interferometer) (23), evaluating unit, dichroic mirror 25 and energy source producing an energy source light 27 for heating the sample 26.

Figure 3:
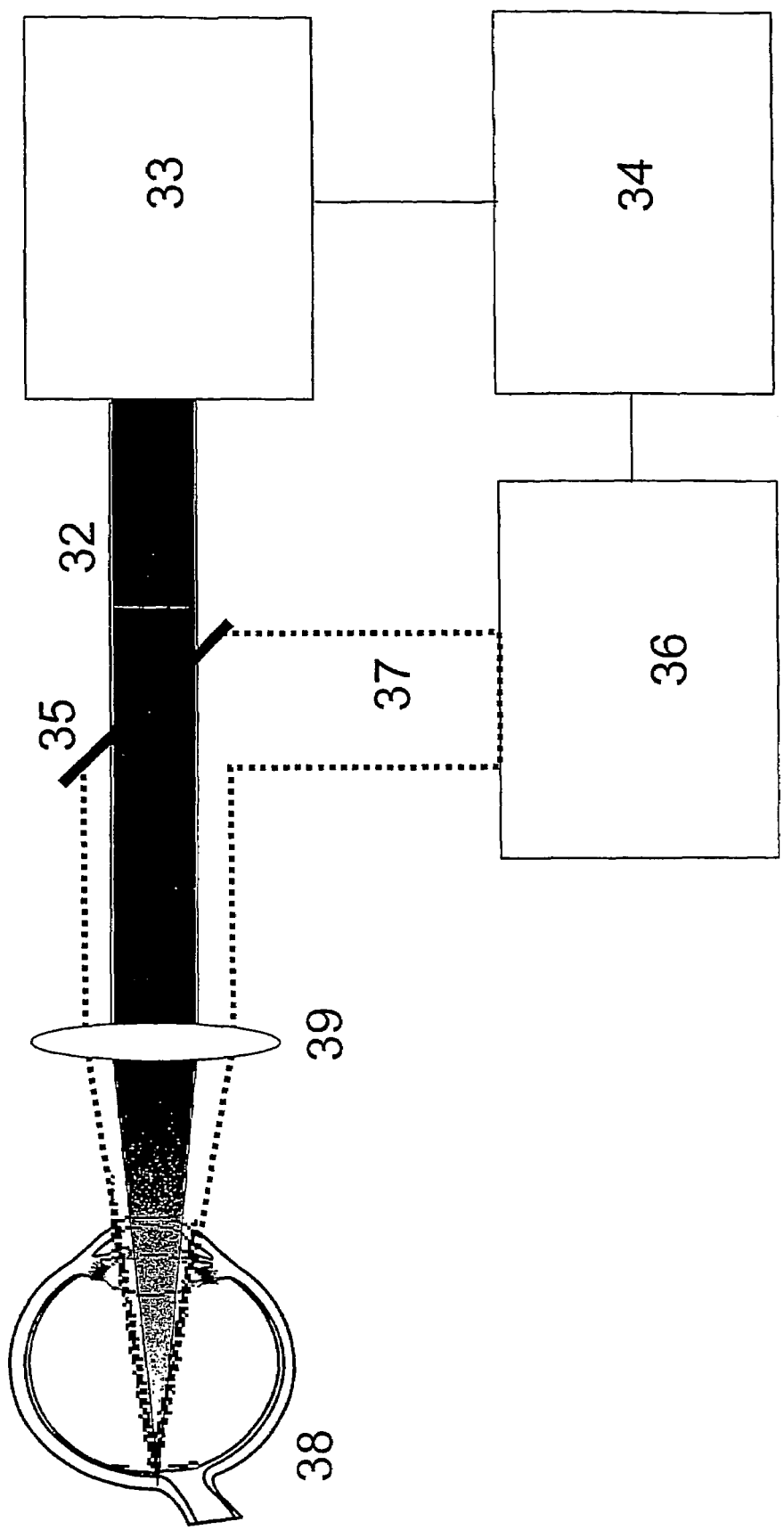
FIG. 3 The diagrammatic structure of the device for determining and controlling the temperature of biological tissue, here the retina of the eye (38), accompanied by irradiation with laser light.

In FIG. 3 a dichroic mirror 35 combines the measuring beam 32 and the light beam 37 of the energy source 36 and this is focussed using imaging optics 39 onto the target area of the retina 38. The test data are recorded by analyzer 33 and evaluated by evaluating unit 34. If need be the energy source 36 can be monitored and controlled by the evaluating unit 34.

Figure 4:
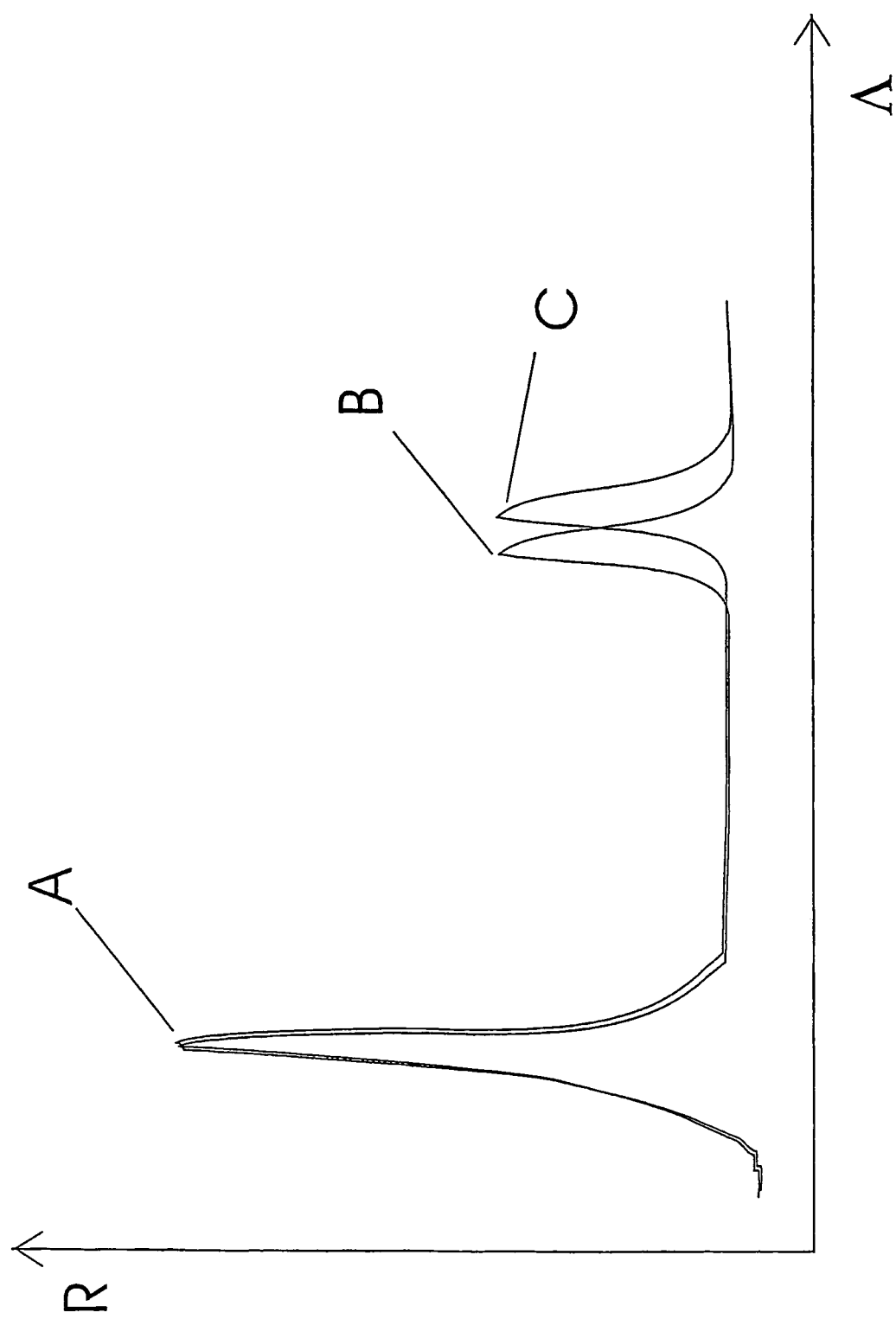
FIG. 4 A typical OCT test signal of a reflecting sample layer for different temperatures T1 and T2.

In FIG. 4 the reflected intensity R is shown against the optical wavelength A with reflection signals from the leading edge of the sample layer (A) and the trailing edge for T1 (B) and T2 (C). The temperature change can be determined from the displacement of the optical path length through the temperature-caused change to the refractive index.

Figure 5:
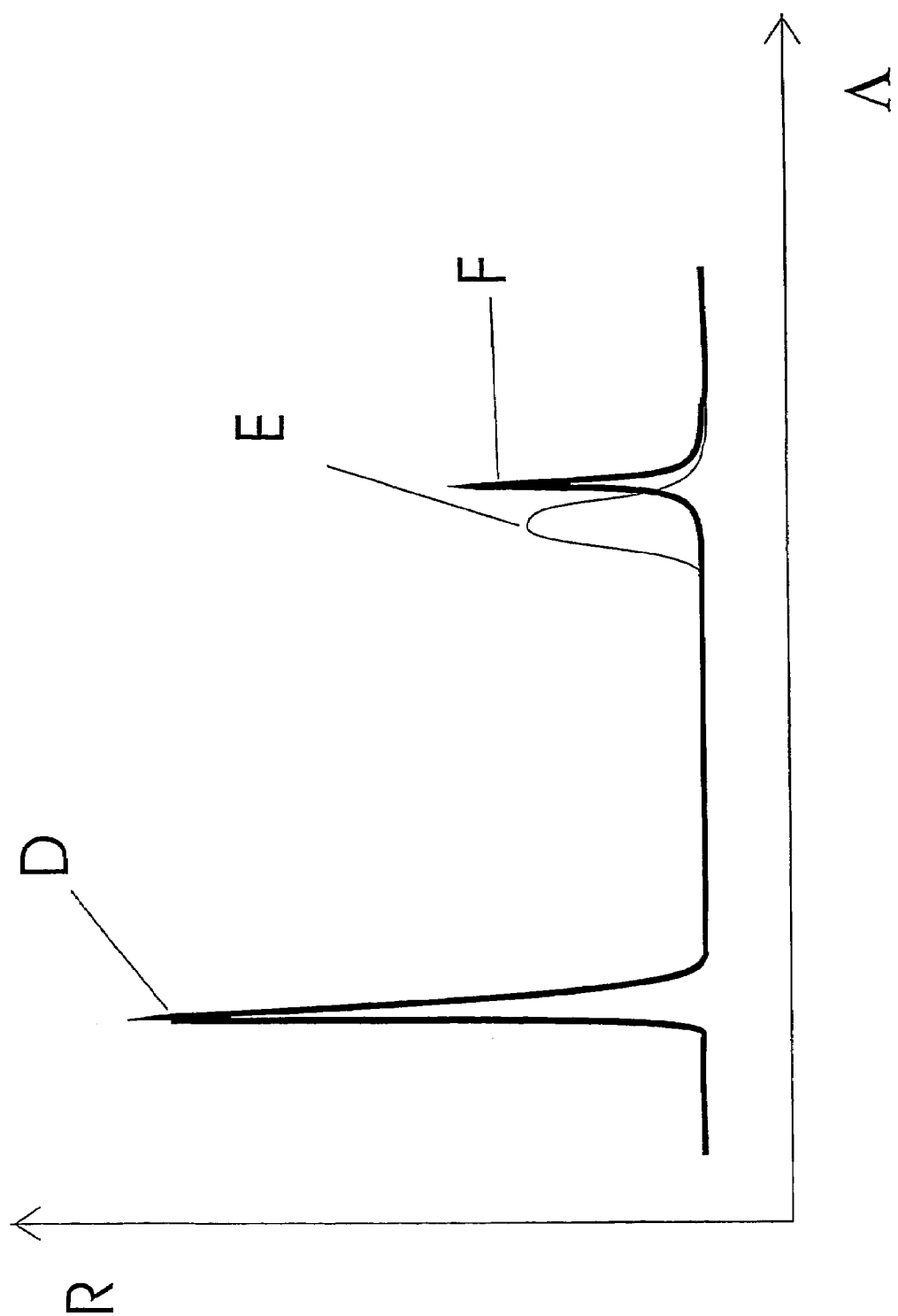
FIG. 5 A representation corresponding to FIG. 4 with reflection signals from the sample layer.

FIG. 5 shows the reflection signals from the leading edge of the sample layer and the trailing edge for T1 (F) and T2 (E). As a result of the temperature-caused refractive index change, there is on the one hand an optical displacement and on the other a widening of the reflection signal by a change to the group refractive index.

As a result of the temperature dependence of the refractive index of a sample 11, 21, 38, with a temperature change there is a modification of the optical path length in the sample. Using an optical measuring beam 12, 22, 32, this can be determined in contactless manner by an analyzer 13, 23, 33, such as e.g. an OCT or some other interferometric device. The sample temperature can be determined from the "optical displacement" obtained of the depth-resolved signals (FIG. 4).

For evaluation at absolute temperatures, it is necessary to determine the temperature dependence of the refractive index in calibration measurements. If the sample thickness is known, e.g. from the OCT signal of the optical analyzer 13, 23, 33 with the aid of a calibration table, it is possible for the evaluating unit 14, 24, 34 to directly determine the sample temperature. For this purpose use is made for evaluation purposes of light reflections on the leading and trailing edges of the sample 11, 21, 38 (FIG. 4). If the sample thickness is unknown, a normalization signal can be obtained beforehand by a reference measurement at a known temperature and can be inputted into the evaluating unit 14, 24, 34.

In the case of scattering samples, the speckle pattern produced by the scatter can be used for evaluating the temperature-induced, optical displacement.

Besides the optical displacement of reflection signals, the line widening of signals can also be used for temperature determination purposes (FIG. 5). As a function of the spectral width of the probing light emitted inter alia by the optical analyzer 13, 23, 33 (e.g. OCT), it is possible in this way to determine a temperature-caused change to the group refractive index.

Specifically in the case of aqueous, i.e. particularly biological samples, account must be taken of the thermal expansion of the sample on heating. Although in the case of water the refractive index decreases with the temperature, which leads to a shortening of the optical light path, at the same time the sample dimensions increase due to thermal expansion and thus bring about a partial compensation of the observable effects of a temperature rise in the interference pattern. Biological tissue is admittedly similar in its optical characteristics to water, but mechanically behaves differently. It does not expand in random manner as a result of its internal cohesion and instead reacts, in part also with a tissue fluid pressure rise. However, the optical refractive index of water is also dependent on the pressure.

Therefore for aqueous samples, the evaluating unit 14, 24, 34 must contain previously known information regarding the thermal expansion behaviour, such as in the form of a stored table, and take account of the same. The production of such tables can take place empirically for specific sample types. In simple physical cases (e.g. defined liquids in dishes), use can also be made of theoretical models.

In an advantageous development of the invention the actual sample temperature measurement does not take place solely by directly converting measured values, but instead by parameter extraction from a numerical modelling of the sample, which takes account of all the known characteristic quantities (temperature and pressure-dependent refractive index, thermal expansion coefficient, elastic tissue parameters, etc.) and links these together in a simulation of the entire measuring process. The result of such a simulation is a theoretical interference pattern, which is brought into optimum coincidence by systematically varying the model (trial and error).

Comparable methods are known in geology when evaluating seismic measurements. With modern microprocessors a transformation for limited targets, i.e. for temperature determination only, is also possible in real time.

The inventive method can be specifically used for determining the laser-induced temperature change in the case of laser irradiation 37 of the retina 38. Evaluation takes place from the OCT signal of reflections from the leading edge of the retina and the reflection signal of the strongly scattering, retinal pigment epithelium (RPE).

As the layer thickness of the retina fluctuates in intra and inter-individual manner, prior to irradiation a reference signal is recorded at known temperature (body temperature). The heat in the retina produced by laser irradiation leads to a change to the retina refractive index.

This refractive index change can be detected with the measuring beam 32 and in the OCT signal leads to the optical displacement of the reflection signal of the retina trailing edge and optionally to a line widening of the signal due to a change to the group refractive index (FIG. 5). These changes can be measured with the analyzer 33 and further processed with evaluating unit 34. The evaluating unit 34 can then control the energy source 36 or switch off on reaching a threshold temperature.

The inventive method is usable for determining the temperature of random samples, such as normally arise in non-destructive material testing. The prerequisite for the usability of the method is the presence of two reflectors for the probing light (e.g. interfaces), in such a way that ideally one partial beam traverses the sample and another does not, whilst the sample must also be largely transparent to the probing light.

Interesting applications occur wherever contactless temperature determination with respect to infrared light emission is not or is only difficultly possible and where the use of temperature sensors in thermal contact is forbidden or undesired, e.g. aqueous solutions under inert gas atmosphere, particularly also aggressive liquids (e.g. hydrofluoric acid) or medical preparations which are to be maintained antiseptic.

What is claimed is:

1. A method for determining the temperature of a biological sample, the method comprising:
    a) directing a probing light beam onto the sample, at least two partial beams of the probing light beam passing through at least two separate long path lengths in the sample, the at least two partial beams reflected or backscattered from at least two different depths in the sample;
    b) employing an interferometric device and one beam of the probing light beam as a reference light beam to produce an interference pattern in an analytical unit;
    c) directing the interference pattern to an evaluating unit;
    d) evaluating the interference pattern in the evaluating unit by comparing a signal intensity of the reflected or backscattered partial beams with an optical path length in the evaluating unit to determine a temperature displacement and a sample temperature from the temperature displacement of the signal intensity.

2. The method according to claim 1, wherein the probing light beam is directed onto a biological tissue.

3. The method according to claim 2, wherein the probing light beam is directed onto a retina of an eye.

4. The method according to claim 1, wherein the employed probing light is laser induced.

5. The method according to claim 1, wherein the probing light beam is a short coherence length light split into a reference beam and a sample beam with a dichroic mirror.

6. The method according to claim 1, wherein a group refractive index of the sample is determined in the evaluating unit by evaluating the interference pattern and determining a different spectral distribution of the partial beams of the probing light beam.

7. The method according to claim 1, wherein the evaluation of the interference pattern takes place by a parameter extraction from a computer-assisted simulation of a measurement by comparing a simulated and a measured interference pattern.

8. The method according to claim 1, wherein calibrating the evaluating unit is carried out at time $t^1$ by a reference measurement at a known temperature.

9. The method according to claim 1, wherein the probing light beam is directed onto an aqueous solution sample.

* * * * *